(12) United States Patent
Morris et al.

(10) Patent No.: US 8,835,710 B2
(45) Date of Patent: Sep. 16, 2014

(54) ANIMAL MODEL FOR INFANT PATHOLOGIES

(75) Inventors: Kristin Morris, Evansville, IN (US); Eduard Poels, Newburgh, IN (US); Hugh Tucker, Brevard, NC (US); Peggy Robertson Borum, Gainesville, FL (US)

(73) Assignee: Mead Johnson Nutrition Company, Glenview, IL (US)

( * ) Notice: Subject to any disclaimer, the term of this patent is extended or adjusted under 35 U.S.C. 154(b) by 918 days.

(21) Appl. No.: 12/409,901

(22) Filed: Mar. 24, 2009

(65) Prior Publication Data
US 2010/0249037 A1    Sep. 30, 2010

(51) Int. Cl.
*A01K 67/00* (2006.01)
*A61B 5/00* (2006.01)
*G09B 23/28* (2006.01)
*G09B 23/36* (2006.01)

(52) U.S. Cl.
CPC ............... *A61B 5/00* (2013.01); *G09B 23/281* (2013.01); *A61B 5/412* (2013.01); *G09B 23/36* (2013.01); *A01K 2267/03* (2013.01); *A61B 2503/40* (2013.01); *A61B 2503/045* (2013.01)
USPC .................................................. 800/9; 800/8

(58) Field of Classification Search
None
See application file for complete search history.

(56) References Cited

U.S. PATENT DOCUMENTS

| | | | |
|---|---|---|---|
| 4,794,105 | A | 12/1988 | Hasegawa et al. |
| 5,336,248 | A | 8/1994 | Good et al. |
| 5,625,124 | A | 4/1997 | Falk et al. |
| 7,148,199 | B2 | 12/2006 | Neu et al. |
| 2002/0002277 | A1 | 1/2002 | Maliszewski et al. |
| 2004/0191170 | A1 | 9/2004 | Mond et al. |
| 2005/0070479 | A1 | 3/2005 | Steinmetzer et al. |
| 2006/0179499 | A1 | 8/2006 | Tirabassie et al. |
| 2007/0054866 | A1 | 3/2007 | Neu et al. |
| 2007/0079390 | A1 | 4/2007 | Rajakumar et al. |

OTHER PUBLICATIONS

Roberto et al. Curr Eye Res 1996;15:932-7.*
Dyess et al. J Surg Res 1995;59:29-34.*
Pak et al. J Korean Med Sci 2002;17:663-8.*
Lodha et al. Pediatr Radiol 2005;35:713-6.*
Toffaletti et al. Aneth Analg 2007;105(6 Suppl):S5-9.*
"A Neonatal Piglet Model of Intraventricular Hemorrhage and Posthemorrhagic Ventricular Dilation," Journal of Neurosurgery: Pediatrics, vol. 107, pp. 126-130 (2007) by Aquilina et al.
"Development of the Retinal Circulation in the Pig," Anatomy and Embryology, vol. 192: 527-536 (1995) by De Schaepdrijver et al.
"Development of the Retina in the Procine Fetus a Light Mocroscopic Study," Anatomia, Histologia, Embryologia, vol. 19: 222-235 (1990) by De Schaepdrijver et al.
"Developing a long-term surviving piglet model of neonatal hypoxic-ischemic encephalopathy," Neurological Research, 2005, vol. 27 pp. 18-21 by McCulloch et al.
"Mechanisms of Hyperoxia-Induced Reductions in Retinal Blood Flow in Newborn Pig," Exp. Eye Res. (1998), 67, 357-369, Article No. ey980535, by Zhu et al.
"Morphologic and Clinical Study of the Retinal Circulation in the Miniature Pig. B: Fluorescein Angiography of the Retina," Exp. Eye Res. (1992) 54, 975-985, by De Schaepdrijver et al.
"Vascular System of the optic nerve head and retina in the pig," Br. J. Ophthalmol. 1971; 55; 808-819, by J. Rootman. Downoaded from bjo.bmj.com.
"Morphologic and Clincal Study of the Retinal Circulation in the Miniature Pig. A: Morphology of the Retinal Microvasculature," Exp. Eye Res. (1992) 54, 965-973, by Simoens et al.
Haase, et al., "Resuscitation with 100% Oxygen Causes Intestinal Glutathione Oxidation and Reoxygenation Injury in Asphyxiated Newborn Piglets," Ann. Surg. Aug. 2004, vol. 240, No. 2: p. 364-73.
Sangild, Per T., Gut Responses to Enteral Nutrition in Preterm Infants and Animals Exp. Biol. Med. 2006. vol. 231, No. 11, pp. 1695-1711.
Smith, et al., "Oxygen-Induced Retinopathy in the Mouse" Invest. Ophthalmol. Vis. Sci. Jan. 1994. vol. 35, No. 1, pp. 101-111.

* cited by examiner

*Primary Examiner* — Janice Li
(74) *Attorney, Agent, or Firm* — Waddey & Patterson, P.C.; James R. Cartiglia

(57) ABSTRACT

A method of providing an animal model for at least one infant pathology, including delivering an animal prior to full physical development; performing a surgical procedure on the animal to provided capacity for respiratory assistance and nutrition; exposing the animal to varying concentrations of oxygen; and optionally repeating the exposure of the animal to varying concentrations of oxygen until the desired condition develops.

14 Claims, No Drawings

ANIMAL MODEL FOR INFANT PATHOLOGIES

BACKGROUND OF THE INVENTION

1. Technical Field

The present invention relates to an animal model for infant pathologies including a model for infants in a neonatal intensive care unit (NICU) setting. More particularly, the present invention relates to a non-human animal model which may be used as a model of retinopathy of prematurity (ROP) as well as for other NICU applications. The invention includes both the non-human models and the process for making specific models.

2. Background Art

There are currently a variety of animal models useful for the study and analysis of diseases as they pertain to humans. Generally, animal models are non-human animals having some type of disease, genetic alteration or conditioning so that the model displays a pathology or ailment similar to a human condition. Through the use of animal models, observations, studies and research may be conducted on diseases and other conditions using methods which might be considered inappropriate for use on humans. Ideally, such science may cultivate new procedures and treatments for humans based upon studies and experiment with the animal models.

For an animal to serve as a useful model, the disease or pathology that the animal model has must be similar in etiology and function to the human equivalent disease or pathology. As different animals display different similarities and dissimilarities to humans, care must be taken in selecting the appropriate animal model for a specific human disease. With this understood, providing the appropriate animal models for the variety of diseases afflicting humans have fostered a great interest. For example, in Falk et al. (U.S. Pat. No. 5,625,124) a transgenic non-human animal is disclosed as a model for the *H. pylori* infection of epithelial cells of the stomach and small intestines. According to Falk et al. the transgenic mouse may be made by constructing a transgene which includes a gut epithelial cell specific promoter and a nucleotide sequence encoding a human fucosyltransferase. The model is also described for use in screening and evaluating compounds which block *H. pylori* adhesion to the gut endothelium or ameliorate the effects of *H. pylori* binding on the pathogenesis of acid peptide disease.

In published U.S. Patent Application No. US 2004/0191170 issued to Mond et al., an animal model is disclosed for evaluating infections caused by enteric pathogens, including diarrheagenic *Escherichia coli*, such as enterotoxigenic, enterohemorrhagic, Shiga-toxin producing, and interopathogenic *E. coli*. The animal model is described as preferably useful for evaluating the efficacy of vaccines and therapeutic agents against enteric bacterial infections as well as for enteric viral infections. Furthermore, Mond et al. describes suitable animals for the animal model as including rodents and rodent like animals such as mice, hamsters, rabbits, guinea pigs, ferrets, chinchillas, and rats.

Tirabassie et al. (published U.S. Patent Application No. US 2006/0179499) provides methods for generating a non-human animal model for a diabetic complication. Generally, animals are administered a TLR agonist in an amount sufficient to induce at least one diabetic complication. Tirabassie et al. further describes an additional aspect of the invention as a method of screening for a therapeutic agent for treating or preventing a diabetic complication which involves the use of a test animal in comparison to a control animal wherein the test animal is provided with at least one diabetic complication and compared to the control animal throughout trials with a therapeutic agent.

In published U.S. Patent Application No. US 2007/0079390 to Rajakumar et al., an animal model is provided which is described as exhibiting neuropathological and behavioral features associated with human schizophrenia. The schizophrenia animal model as described by Rajakumar et al., is made by a method comprising the premature elimination of subplate cells in the developing prefrontal cerebral cortex of the animal.

According to Aquilina et al. in "A Neonatal Piglet Model Of Intraventricular Hemorrhage And Posthemorrhagic Ventricular Dilation," JOURNAL OF NEUROSURGERY: PEDIATRICS, Vol. 107, pages 126-130 (2007), piglets are created to replicate human neonatal intraventricular hemorrhage (IVH) and posthemorrhagic ventricular dilation (PHVD). Such models allow for physiological and ultrasonographic monitoring over a prolonged survival period so as to evaluate both non-invasive and surgical options in the management of both IVH and PHVD in young humans.

One area in which there has been minimal research with animal models is in simulating the conditions of an infant within a neonatal intensive care unit (NICU). NICUs typically specialize in the care of ill or preterm newborn infants by use of specialized equipment and unique technologies. In addition to prematurity, NICUs provide treatment for infants with diseases including perinatal asphyxia, major birth defects, sepsis, respiratory distress syndrome, hypoxia, intraventricular hemorrhage, neonatal seizures, brain insult, neurodegeneration, and retinopathy of prematurity and the like.

In particular, retinopathy of prematurity (ROP) afflicts over 300,000 infants worldwide. In attempts to both treat and inhibit ROP which can potentially lead to blindness, technologies have been created for the disease. Specifically, in U.S. Pat. No. 5,336,248, issued to Good et al, an apparatus for the treatment or inhibition of retinopathy of prematurity is provided which provides substantially red light having a wave band of approximately 612 nanometers to the infant. As a result the infant is restricted to red light which Good et al. believes is beneficial in the treatment of the disease.

In Neu et al (U.S. Pat. No. 7,148,199), dipeptides are administered which may prevent retinal blood vessel damage, a common characteristic of retinopathy. Moreover, Neu et al. describes the use of peptides as preventing the proliferation of abnormal blood vessels through the administration of arginine and glutamine typically in an aqueous solution.

Despite there being a variety of animal models specific to different human diseases, there are few, if any, animal models available for pathologies associated with infants in a NICU. Rather, the majority of animal models is linked to adult diseases and only occasionally correlates to infant conditions of the same disease. In addition, there are few resources available for the study of ROP even though the disease affects thousands of infants.

What is desired therefore is an animal model that could be used for simulating the conditions of various diseases that afflict human infants. In addition, there is a need for an animal model which simulates ROP. Further desired is an animal model which may be used to mimic diseases of infants that are characterized as NICU applications. Indeed, a combination of characteristics including an animal model which replicates ROP of a human infant provides an animal model useful as a tool in both observing and treating pathologies of infants that are treated in the NICU.

SUMMARY OF THE INVENTION

The present invention provides an animal model for simulating infants having pathologies which are typically treated in a NICU setting. In embodiments of the invention, the animal model may be used to mimic retinopathy of prematurity, hypoxia, NEC, sepsis, respiratory distress syndromes, intraventricular hemorrhage, neonatal seizures, brain insult, neuro-degeneration, and the like.

In recent years, there has been a significant increase in survival of very premature infants due to advances in medical technology. Ironically, significant eye damage is more likely due to the increased survival rate of the premature infants due to the occurrence of ROP. Generally, ROP occurs in over about 15% of all premature births, with over 2,000 children annually having ROP in the United States alone. ROP is typically defined as a retinal blood vessel disorder that occurs during the development of the premature infant's eyes. Under normal gestation the blood vessels of the infant's eye grow from the back central portion of the eye out to the edges of the eye. Conversely, in premature infants this developmental process does not completely occur, which may lead to an abnormal blood vessel arrangement and scar tissue. In worse cases, retinal detachment may occur and complete blindness is possible.

Advantageously, a piglet may be used for the animal model for ROP of the present invention as the porcine eye shares remarkable similarities with a human eye. In "*Development Of The Retinal Circulation In The Pig*," ANATOMY AND EMBRYOLOGY, Vol. 192: 527-536 (1995) De Schaepdrijver et al. describes the porcine eye and the human eye as having a great resemblance, thus making the pig useful for ophthalmological research. This is further reinforced in "*Development Of The Retina Into Procine Fetus A Light Microscopic Study*," ANATOMIA, HISTOLOGIA, EMBRYOLOGIA, Vol. 19: 222-235 (1990) also by De Schaepdrijver et al., where the porcine eye is discussed for use in human retina research. Advantageously, the similarity of the porcine eye to a human eye provides the opportunity to replicate ROP as seen in human infants in an animal model which closely replicates human infants having ROP. More particularly, a piglet may be created to have ROP so that observations and studies may be made so as to help treat and inhibit ROP in infants.

Generally, by practice of the present invention, a preterm piglet may be delivered prior to full physical development and subsequently exposed to varying concentrations of oxygen to develop retinopathy in the model piglet. In further embodiments, animal models may be created to simulate conditions of the human infant in a NICU by delivering the animal prior to full physical development and subsequently exposing the animal to varying concentrations of oxygen and observing for specific pathologies. Thus, the use of a model piglet or other non-human animal within the present invention extends to other pathologies typically treated within the NICU.

The inventive method of providing a piglet model for retinopathy may include the delivery of a preterm piglet delivered at about 80 days to about 120 days gestation and the subsequent monitoring of at least one physiological condition which may include monitoring of the oxygenation status via a pulse oximeter. The piglet may further be subjected to surgical procedure to provide capacity for both respiratory assistance and nutrition in order to sustain the piglet's survival throughout the study and development of the model. Subsequently, the piglet may be exposed to varying concentrations of oxygen, including oscillating low and high concentrations of oxygen for about 2 hours to about 6 hours in duration. The oxygen exposure may continue until the desired pathology is created.

In creating the piglet model for ROP, the piglet may undergo additional surgeries including the catheterization of the piglet for both the sampling and administering of substances. The piglet may be catheterized with an external jugular catheter for blood sampling and in further embodiments may be catheterized with a carotid catheter which may be threaded towards the aorta for parenteral nutrition. In even further embodiments, the catheterization may include gastric catheterization as well as bladder catheterization for the administration of therapeutic agents and the monitoring of metabolites produced by the piglet model. In producing the piglet model of retinopathy, the varying concentrations of oxygen may include both low and high concentrations of oxygen where the piglet may be exposed to high concentrations of oxygen for about a total time of about 30 minutes to about 90 minutes prior to examining the piglet and continuing exposure. Further embodiments include the exposure of the model piglet to varying concentrations of oxygen at about 12 hours to about 48 hours after the piglet is delivered. Upon producing the piglet model, subsequent observations and administrations of therapeutic agents may be initiated so as to provide further study regarding human infants having ROP.

An object of the invention therefore is a method of providing a piglet model for retinopathy including providing a piglet and exposing the piglet to varying concentrations of oxygen.

Still another object of the invention is a method of providing a piglet model for retinopathy providing a preterm piglet delivered prior to full physical development and monitoring at least one physiological condition throughout the development of retinopathy in the model piglet.

Another object of the invention is a piglet model for ROP.

A further object of the invention is a method of simulating conditions of the human infant in a NICU comprising the steps of providing a preterm animal and exposing the animal to varying concentrations of oxygen to provide pathologies to the animal that are associated with a human infant in a NICU.

These aspects and others that have become apparent to the skilled artisan upon review of the following description can be accomplished by providing a preterm piglet having been specifically subjected to varying concentrations of oxygen to provide a desired pathology. The piglet model for retinopathy advantageously provides a model mimicking a human infant eye with similar physiological characteristics of ROP. The model may additionally be used to mimic other NICU applications by subtle manipulations to the exposure to varying concentrations of oxygen including hypoxia, NEC, sepsis, respiratory distress syndromes, intraventricular hemorrhage, neonatal seizures, brain insult, and neuro-degeneration and combinations thereof.

It is to be understood that both the foregoing generally description and the following detailed description provide embodiments of the invention and are intended to provide an overview or framework of understanding to the nature and character of the invention as it is claimed.

DETAILED DESCRIPTION OF THE PREFERRED EMBODIMENTS

Definitions

As used herein, the term "infant" means a person not more than 12 months of age.

A "preterm infant" is an infant born at less than about 37 weeks gestation.

A "full term infant" as used herein, means an infant born after at least about 37 weeks gestation.

A "premature infant" as used herein, is another term for a preterm infant.

"Children" are defined as humans over the age of about 12 months to about 12 years old.

An "animal model" as used herein comprises a non-human animal that has a pathology, condition or characteristic similar to a human pathology condition or characteristic.

A "preterm piglet" as used herein means a piglet delivered at less than about 100 days gestation.

A "therapeutically effective amount," as used herein is generally defined as an amount of a therapeutic agent that provides an observable result within the subject administered thereto.

The term "simulating," as used herein means having or taking the form or appearance of or having or producing a symptomatic resemblance to.

Invention

In the practice of the present invention, an appropriate animal is selected for the animal model based upon the desired pathology or condition that is to be observed. Animals for the animal model may include rodents, such as rats or mice, as well as other animals including guinea pigs, hamsters, sheep, non-human primates or pigs. Pigs, also referred to as hogs, or swine, are defined as any even-toed ungulates within the family Suidae. Pigs possess eyes with anatomical features similar to human eyes and thus are suitable for use in the study of retinopathy.

In providing a preterm piglet for a piglet model for retinopathy, a piglet is delivered prior to full physical development. The piglet is delivered early so as to provide the piglet prior to full retinal vascular development. The appropriate time for delivery is from about 80 days to less than about 100 days gestation as the average full term gestation for a piglet is approximately 112 to about 114 days. In other embodiments, the piglet is delivered at about 100 days gestation, although it may be delivered earlier or later depending on the desired retina development of the piglet. Preterm delivery may conducted through a cesarean section, induced vaginal birth or by other methods for obtaining a preterm piglet prior to the full term average gestation for pigs.

Upon providing the preterm piglet, the oxygenation status of the piglet may be monitored via a pulse oximeter. Generally, the pulse oximeter will be utilized to display the percentage of arterial hemoglobin in the oxyhemoglobin configuration and is generally considered useful for monitoring the piglet's well being. Advantageously a pulse oximeter can provide a rapid response to changes in the blood oxygenation while not requiring invasive surgery.

In further embodiments, other physiological conditions of the piglet may be monitored so that the status of the piglet is understood throughout development of the model.

In maintaining the survival of the piglet for observation, capacity may be provided to the piglet for both respiratory assistance and nutrition. In providing respiratory assistance, a ventilator may be used with the piglet. Generally, a ventilator for use in practice of the present invention may be defined as any type of machine designed to mechanically move air into or out of the animal's lungs and essentially provide the mechanism of breathing for the animal. Both invasive and non-invasive ventilator models may be utilized wherein either a nasal mask or intubation may be used in providing air for the animal model. Nutrition may be provided to the animal by way of parenteral nutrition wherein the animal is fed intravenously thus bypassing both eating and digestion. More specifically, the animal model may be provided a nutritional composition including salts, amino acids, glucose, protein, fats and lipids and added vitamins and minerals for sustaining the animal during the development and study. In providing parenteral nutrition for a piglet, a carotid catheter may be inserted toward the aorta for nutrition. In further embodiments, an infusion pump may be utilized to deliver the nutritional fluid to the animal. Catheterization may occur at various locations, including the subclavian veins or jugular veins or alternatively, in various peripheral veins of the animal.

In further embodiments of providing a piglet model for retinopathy, a jugular catheter may be utilized for blood sampling. This may include jugular catheterization through a venipuncture method where infrequent punctures may be utilized for sampling blood. In further embodiments, a catheter may be inserted into the jugular vein requiring the jugular vein to be exposed for ligation. In even further embodiments, the jugular of piglet may be catheterized via a non-surgical method utilizing a catheter and dilator within the jugular vein. In certain embodiments a small incision may be made over the right jugular vein of a piglet with the subcutaneous tissue cleared away for exposing the vein for catheterization. The catheter may be subcutaneously positioned within the vessel and secured in place with the incision substantially closed with access to the catheter remaining. In the practice of the present invention, multiple types of jugular catheters may be used, including both external and internal catheters in providing samples of blood from the animal model.

Other types of catheterization may include the use of a gastric catheter for the purpose of administering therapeutic agents to the piglet. Therapeutic agents such as dipeptides may be administered to the piglet via the gastric catheter for the purposes of observation and study. The gastric catheter may be inserted by a Stamm Gastrostomy or through an open gastrostomy when either method provides an opening directly into the stomach. Additional embodiments may provide for the piglet or other animal to be administered nutritional media in addition to or instead of therapeutic agents. In other embodiments, therapeutic agents may be enterally administered to the piglet. As used herein, "enterally" or "enteral" means through or within the gastrointestinal, or digestive tract, and "enteral administration" includes oral feeding, intragastric feeding, nasogastric feeding, transpyloric administration, or any other introduction of therapeutic or nutritional agents into the digestive tract.

Additional surgical procedures that may be performed include the placement of a bladder catheter into the piglet so that metabolites may be monitored from the model. More specifically, individuals may assess safety or toxicity data based upon the metabolites realized in the pig's urine.

In creating an animal model having conditions that simulate a human infant in a NICU, the animal may be exposed to varying concentrations of oxygen. More specifically, in creating a piglet model for retinopathy, the piglet may be exposed to oscillating low and high concentrations of oxygen until the desired degree of retinopathy develops. This may include exposure to varying concentrations of oxygen for about two hours to about six hours with a total time of exposure to high concentrations of oxygen being from about 30 minutes to about 90 minutes prior to exposure to a low concentration of oxygen. Generally, the target time for exposure to high concentrations of oxygen is approximately one hour with the total oscillating treatment spanning about four hours though both the time for high concentration of oxygen exposure and total oscillating exposure may be varied depending upon the specific development of the retinopathy within the piglet and the desired physiological state of the piglet model by the observer. Typically, the first exposure to the varying concentrations of oxygen occurs from about 12 hours to about 48 hours after the preterm piglet is delivered. Subsequently, the piglet may be subjected to varying concentrations of oxygen for additional cycles with each cycle being from about two hours to about six hours.

Subsequently, the piglet may be subjected to varying concentrations of oxygen for additional cycles with each cycle being from about two hours to about six hours. This may occur after the piglet has been examined for signs of development of retinopathy, so that if further development is required, the piglet may be exposed to varying concentrations of oxygen for additional cycles. Generally, the repeated exposure of the piglet to varying concentrations of oxygen may repeatedly for a time period of less than about 10 days from the delivery date of the piglet. Preferably, the piglet may be examined at various points to assess whether or not the retina has developed to the desired retinopathy. Most often the study is limited to about less than 12 days and more likely about nine days from the delivery of the piglet as survival is difficult to maintain without continuous mechanical ventilation.

Upon developing the piglet model, observations, studies and research can be conducted that may be useful for infants with ROP. Specifically, efficacy studies for therapeutic agents may be undertaken which can include the administration of dipeptides. Additionally, experimental surgical procedures to repair the porcine eye afflicted with retinopathy may be attempted in hopes of better treating the disease in infants born with ROP.

Although an animal model is disclosed for mimicking ROP, manipulations in the oxygen exposure may render the model appropriate for other NICU applications, including hypoxia, NEC, sepsis, respiratory distress syndromes, intraventricular hemorrhage, neonatal seizures, brain insult, neuro-degeneration, and the like. Furthermore, different animals may be used for the animal model as different animals may more closely simulate the many physiological attributes of an infant in the NICU.

Through the use of the aforementioned steps including the exposure to varying concentrations of oxygen, a piglet model for retinopathy is obtained, which simulates ROP in an infant closer than other animal models. The model can establish the progression of retinal vascularization in eyes from normal piglets and from eyes of piglets subjected to conditions to induce retinopathy. Furthermore, retinal examinations can be used to monitor pathological retinal neovascularization, vasoobliteration, reversal of pathological findings and other indices relevant to the development of the retinopathy.

In order to further illustrate the principles and operation of the present invention, the following example is provided. However, this example should not be taken as limiting in any regard.

EXAMPLE

A preterm piglet is delivered at about 100 days via the cesarean method. The piglet's oxygenation status is monitored via a pulse oximeter from about immediately after birth. Subsequently, surgical procedures are conducted to ventilate the piglet, as well as to place an external jugular catheter for blood sampling, a carotid catheter threaded toward the aorta for parenteral nutrition, gastric catheter for administering dipeptides for future experiments, and a bladder catheter for monitoring relevant metabolites for safety/toxicity data for future experiments. Following surgery, the piglet is examined to establish baseline data for the retinas and the parenteral nutrition is initiated. On Day 2, the piglet is exposed to oscillating low, high, low, high concentrations of oxygen for about 1 periods of time for a total of 4 hours of treatment. After the treatment, the retinas of the piglet are examined for development of retinopathy. The oxygen treatments are then repeated unless or until the model is fully developed for the desired retinopathy.

Accordingly, by the practice of the present invention, a piglet model and a method for creating the piglet model having heretofore unrecognized characteristics are provided. These piglet model exhibits characteristic that simulate ROP in an infant in a NICU setting. Furthermore, additional animal models may be created for other NICU conditions including but not limited to hypoxia, NEC, sepsis, respiratory distress syndromes, intraventricular hemorrhage, neonatal seizures, brain insult, neuro-degeneration, and the like.

The disclosures of all cited patents and publications referred to in this application are incorporated herein by reference.

The above description is intended to enable the person skilled in the art to practice the invention. It is not intended to detail all of the possible variations and modification that are apparent to the skilled worker upon reading the description. It is intended, however, that all such modifications and variations be included within the scope of the invention that is defined by the following claims. The claims are intended to cover the indicated elements and steps that any arrangement or sequence that are effective to meet the objectives intended for the invention, unless the context specifically indicate to the contrary.

What is claimed is:

1. A method of providing a piglet model for retinopathy, the method comprising:
   a) providing a preterm piglet with the piglet delivered from about 80 days to less than about 100 days gestation and prior to full physical development;
   b) monitoring at least one physiological condition of the piglet;
   c) performing a surgical procedure on the piglet to provide capacity for respiratory assistance and nutrition;
   d) exposing the piglet to varying concentrations of oxygen for a time period of less than about 12 days from delivery of the piglet; and
   e) optionally repeating the exposure of the piglet to varying concentrations of oxygen until the desired retinopathy develops.

2. The method of claim 1 wherein step b) comprises monitoring the piglet's oxygenation status.

3. The method of claim 2 wherein a pulse oximeter is used for monitoring the piglet's oxygenation status.

4. The method of claim 1 wherein the operating of step c) further comprises ventilating the piglet.

5. The method of claim 1 wherein the operating of step c) further comprises placing a catheter in the piglet.

6. The method of claim 5 wherein the catheter comprises an external jugular catheter for blood sampling.

7. The method of claim 5 wherein the catheter comprises a gastric catheter.

8. The method of claim 5 wherein the catheter comprises a bladder catheter.

9. The method of claim 1 wherein step d) further comprises exposing the piglet to varying concentrations of oxygen for about 2 hours to about 6 hours.

10. The method of claim 1 wherein step d) further comprises exposing the piglet to low and high concentrations of oxygen.

11. The method of claim 9 wherein the piglet is exposed to high concentrations of oxygen for a total time of about 30 minutes to about 90 minutes.

12. The method of claim 1 wherein step d) initiates about 12 hours to about 48 hours after the piglet is delivered.

13. The method of claim 1 further comprising:
a) conducting examinations of the piglet's eyes to observe characteristics relevant to retinopathy.

14. A piglet model for retinopathy made by the steps of claim 1.

* * * * *